(12) United States Patent
Utsch et al.

(10) Patent No.: US 9,113,987 B2
(45) Date of Patent: Aug. 25, 2015

(54) ORAL HYGIENE IMPLEMENT AND ORAL HYGIENE DEVICE

(75) Inventors: Joern Utsch, Eschborn (DE); Thomas Fritsch, Eppstein (DE); Andreas Kramp, Bad Camberg (DE)

(73) Assignee: BRAUN GMBH, Kronberg (DE)

( * ) Notice: Subject to any disclaimer, the term of this patent is extended or adjusted under 35 U.S.C. 154(b) by 438 days.

(21) Appl. No.: 13/557,242

(22) Filed: Jul. 25, 2012

(65) Prior Publication Data
US 2014/0026337 A1 Jan. 30, 2014

(51) Int. Cl.
*A61C 17/34* (2006.01)
*A61C 17/22* (2006.01)
*A61C 17/26* (2006.01)

(52) U.S. Cl.
CPC ........... *A61C 17/3436* (2013.01); *A61C 17/222* (2013.01); *A61C 17/26* (2013.01)

(58) Field of Classification Search
CPC .. A61C 17/222; A61C 17/3481; A61C 17/16; A61C 17/22; A61C 17/3436; A61C 17/349; A61C 17/26; A46B 2200/1066
USPC .......................... 15/21.1, 22.1, 22.3, 22.4, 28
See application file for complete search history.

(56) References Cited

U.S. PATENT DOCUMENTS

| | | | | |
|---|---|---|---|---|
| 2,140,307 | A | * 12/1938 | Belaschk et al. | 15/28 |
| 7,810,201 | B2 | * 10/2010 | Braun | 15/28 |
| 2001/0014990 | A1 | 8/2001 | Fritsch et al. | |
| 2004/0200016 | A1 | * 10/2004 | Chan et al. | 15/22.1 |
| 2005/0011023 | A1 | 1/2005 | Chan | |

FOREIGN PATENT DOCUMENTS

EP 2 229 916 A1 9/2010

OTHER PUBLICATIONS

International Search Report for PCT/IB2012/053791 dated Oct. 5, 2012.

* cited by examiner

*Primary Examiner* — Robert Scruggs
(74) *Attorney, Agent, or Firm* — Vladimir Vitenberg

(57) ABSTRACT

An oral hygiene implement is provided. The oral hygiene implement includes a housing; a movably mounted functional element; a fixation element that is secured at the housing and that essentially locks the functional element at the housing; and an axle that is supported by the fixation element. The functional element is arranged for movement around the axle and the fixation element extends through a cut-out or recess provided in a carrier element of the functional element, such that pulling the functional element out of the housing along the longitudinal axle extension direction is inhibited.

12 Claims, 8 Drawing Sheets

US 9,113,987 B2

ORAL HYGIENE IMPLEMENT AND ORAL HYGIENE DEVICE

CROSS REFERENCE TO RELATED APPLICATIONS

This application claims the benefit of European Patent Convention Application No. 11006101.7, filed Jul. 25, 2012, the substance of which is incorporated by reference in its entirety herein.

FIELD OF THE INVENTION

The present disclosure is directed to an oral hygiene implement and to an oral hygiene device. More particularly, the present disclosure is directed to an oral hygiene implement having a movably mounted functional element that is locked at the housing by a fixation element.

BACKGROUND OF THE INVENTION

It is known to lock a movably mounted functional element at a housing of an oral hygiene implement using a fixation element. For example, in case of replaceable toothbrush refills, the movably mounted brush head may be locked at the housing of the refill by means of a locking pin. The locking pin extends into a recess in the functional element and thus inhibits the functional element from being easily separated from the housing without irreparable damage to at least the housing or the functional element.

It is a desire to provide an oral hygiene implement having a locking functionality that is improved over the prior art or that at least provides an alternative to the known locking concepts.

SUMMARY OF THE INVENTION

In one embodiment, an oral hygiene implement is disclosed. The oral hygiene implement includes a housing; a movably mounted functional element; a fixation element that is secured at the housing and that essentially locks the functional element at the housing; and an axle that is supported by the fixation element. The functional element is arranged for movement around the axle and the fixation element extends through a cut-out or recess provided in a carrier element of the functional element, such that pulling the functional element out of the housing along the longitudinal axle extension direction is inhibited.

These and other features, aspects and advantages of specific embodiments will become evident to those skilled in the art from a reading of the present disclosure.

BRIEF DESCRIPTION OF THE DRAWINGS

The embodiments set forth in the drawings are illustrative in nature and not intended to limit the invention defined by the claims. The following detailed description of the illustrative embodiments can be understood when read in conjunction with the following drawings, where like structure is indicated with like reference numerals and in which:

DETAILED DESCRIPTION OF THE INVENTION

The following text sets forth a broad description of numerous different embodiments of the present disclosure. The description is to be construed as exemplary only and does not describe every possible embodiment since describing every possible embodiment would be impractical, if not impossible. It will be understood that any feature, characteristic, component, composition, ingredient, product, step or methodology described herein can be deleted, combined with or substituted for, in whole or part, any other feature, characteristic, component, composition, ingredient, product, step or methodology described herein. Numerous alternative embodiments could be implemented, using either current technology or technology developed after the filing date of this patent, which would still fall within the scope of the claims. All publications and patents cited herein are incorporated herein by reference.

According to the present disclosure, an oral hygiene implement includes a fixation element for locking a movably mounted functional element with respect to the housing so that the functional element cannot be separated from the housing without incurring irreparable damage to oral hygiene implement. In order to achieve this locking functionality, the fixation element extends through a recess or cut-out (for example, a through hole) provided in the functional element, where the recess or cut-out may in particular be provided in a carrier element of the functional element. In certain embodiments, the fixation element is arranged such that a rotation axis of the functional element extends through the fixation element, in particular wherein an axle extending along the rotation axis is born by the fixation element, where the axle may be fixedly secured at the fixation element or the axle may be floatingly supported by the fixation element such that at least a rotation of the axle around the rotation axis is enabled. In some embodiments, the fixation element is secured at least at two different locations at the housing, for example, where these locations are essentially oppositely arranged at the housing. In some embodiments the fixation element is non-detachably secured at the housing of the oral hygiene implement. In some embodiments, the fixation element extends in a curved manner between two mounting locations. In some embodiments, the fixation element is secured at an inwardly thickened portion of the housing of the oral hygiene implement.

Figure 1:
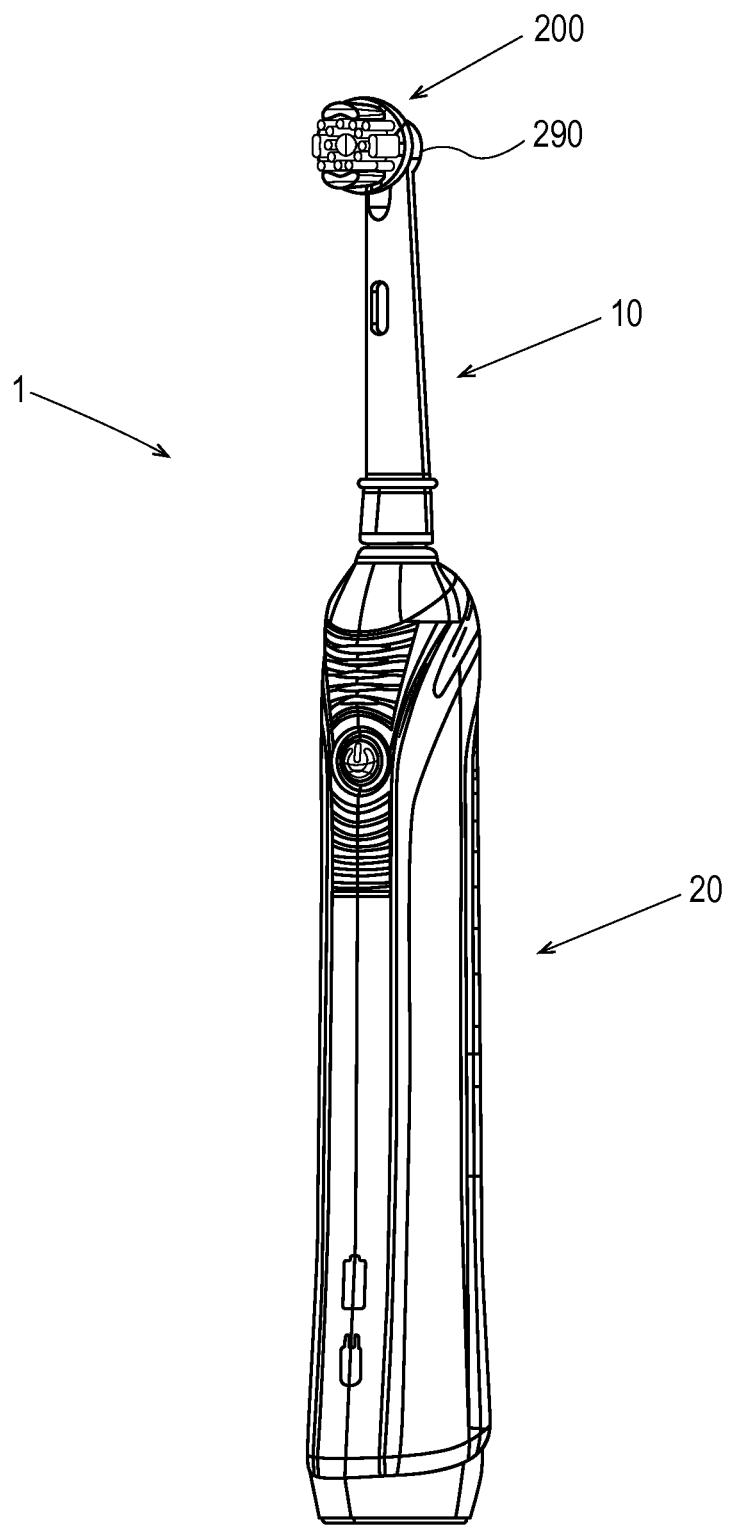
FIG. 1 is a perspective depiction of an example oral hygiene device including an oral hygiene implement.

FIG. 1 is a perspective depiction of an example embodiment of an oral hygiene device 1. In one embodiment, the oral hygiene device 1 may be an electric toothbrush. The oral hygiene device comprises an oral hygiene implement 10 and a handle 20. The oral hygiene implement 10 may be a brush section of the electric toothbrush. The oral hygiene implement 10 may in particular be realized as a detachable attachment for simple replacement with other oral hygiene implements, for example, when the oral hygiene implement 10 is worn out or in case that a different oral hygiene treatment should be performed. The oral hygiene implement 10 has a functional element 200 that is movably mounted at a housing 290 of the oral hygiene implement 10. The functional element 200 is here realized as a brush head having cleaning elements for cleaning teeth and/or massaging gums.

Figure 2:
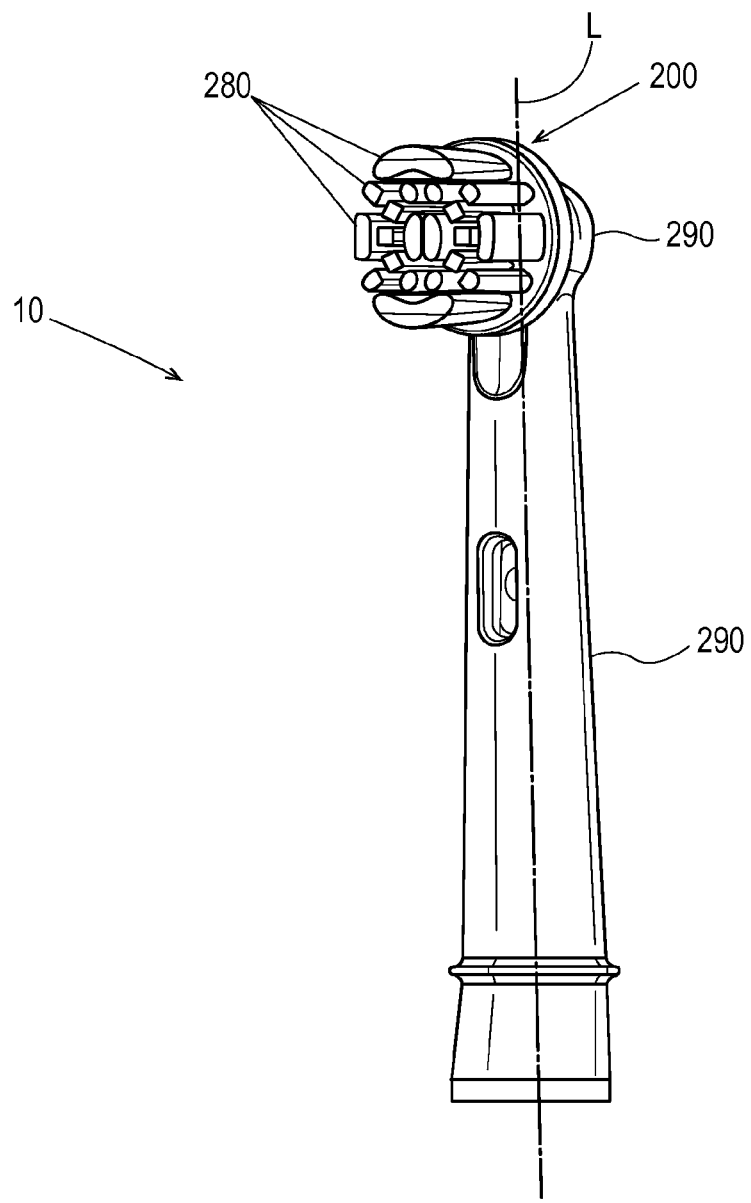
FIG. 2 is a depiction of an example oral hygiene implement according to embodiments shown and described herein.

FIG. 2 is a depiction of an example embodiment of an oral hygiene implement 10 in accordance with at least one aspect of the present disclosure. In one embodiment, the oral hygiene implement 10 may be a detachable attachment. The oral hygiene implement 10 has a movably mounted functional element 200, which may be a brush head having cleaning elements 280 for cleaning teeth and/or massaging gums. The housing 290 of the oral hygiene implement 10 may have an elongated, essentially tubular form that tapers slightly towards the head region. The oral hygiene implement 10 may generally be structured so that it can be entered into the oral cavity while keeping discomfort at a low level and to allow for cleaning of the teeth such as the molars. The oral hygiene implement 10 may have a longitudinal extension axis L and the functional element 200 may be mounted for rotation or oscillatory rotation around a rotation axis R (shown in FIG. 3) that may be essentially perpendicular to the longitudinal extension axis L (while this shall not be interpreted as limiting the possible embodiments of oral hygiene implements in accordance with at least one aspect of the present disclosure).

Figure 3:
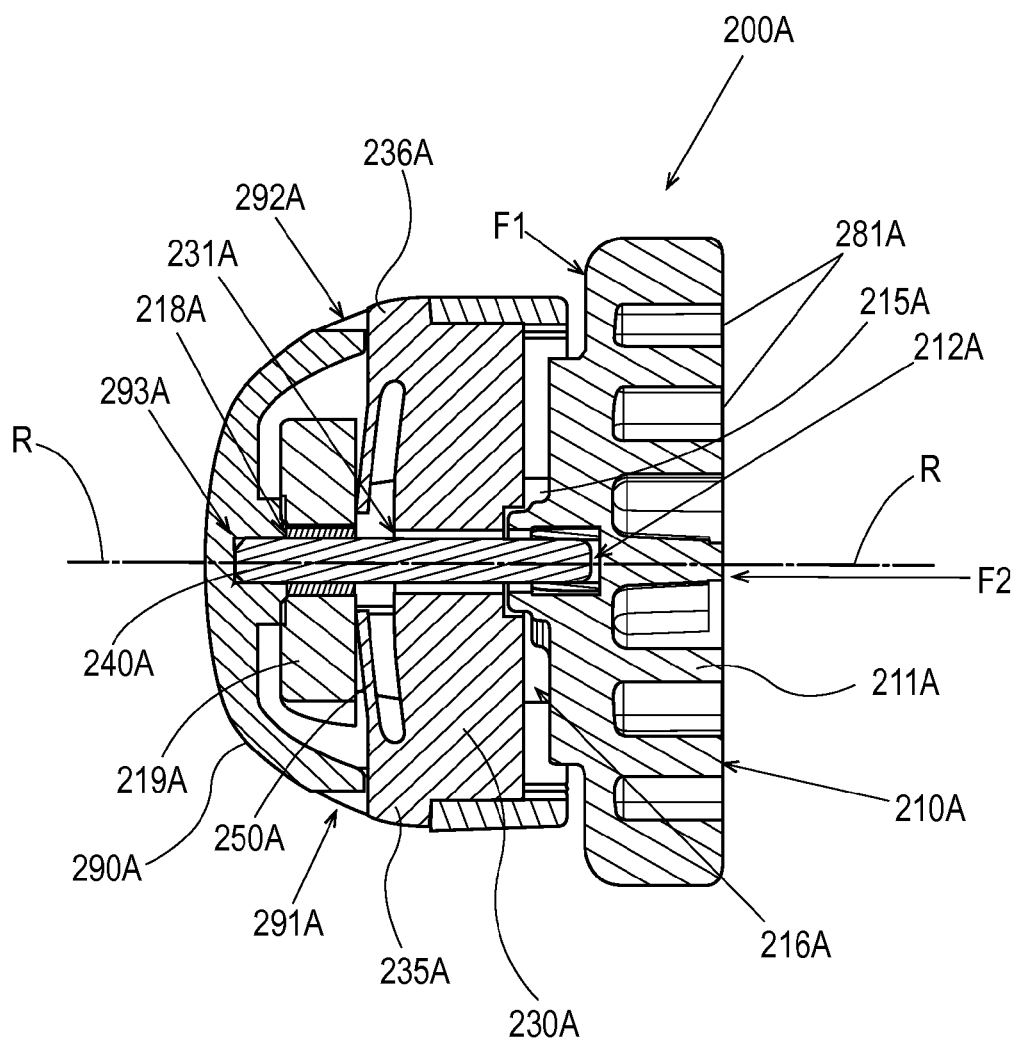
FIG. 3 is a cross sectional cut in a plane perpendicular to a longitudinal extension axis of the oral hygiene implement through a head section of an oral hygiene implement, here shown without cleaning elements that may be arranged in mounting holes provided in a carrier element of a movably mounted functional element.

FIG. 3 is a cross sectional cut through a head region of an example embodiment of an oral hygiene implement, which cross sectional cut is taken such that a rotation axis R lies in the cut plane. A functional element 200A is here shown without cleaning elements as shown in for example, FIG. 2 for simplification of the visualization. The functional element 200A is movably mounted at the housing 290A of the oral hygiene implement such that it can rotate or oscillate around the rotation axis R. The functional element 200A comprises a carrier element 210A.

The carrier element 210A may have a cut-out (for example, a through-hole) or recess 216A through which the rotation axis R extends and through which a fixation element 230A extends. The fixation element 230A has a bore 231A in which an axle 240A that extends along the rotation axis R is supported. In one embodiment, the axle 240A may be press-fitted into the bore 231A. The fixation element 230A may be elongated and may extend in a direction essentially perpendicular to the rotation axis R through the cut-out or recess 216A. Two ends 235A and 236A of the fixation element 230A that may lie oppositely to each other in the elongated extension direction may be realized as snap-noses that are snapped into respective cut-outs 291A and 292A in the housing 290A of the oral hygiene implement. The snap connection may be realized as being non-detachable, i.e. the mounted fixation element 230A then essentially cannot be separated from the oral hygiene implement without any irreversible damages to the oral hygiene implement (i.e. at least one of the housing 290A, the fixation element 230A, or the functional element 200A will suffer irreversible damage). The snap-noses of the fixation element 230A may have 90 degree undercuts that extend into the cut-outs 291A and 292A provided in the housing 290A and thus avoid that the fixation element 230A can be easily separated from the housing 290A when mounted. In another embodiment, the fixation element may be glued to the housing, may be screwed to the housing, may be welded to the housing, etc., i.e. the fixation element may be fixedly secured to the housing. In another embodiment, the fixation element may be detachably secured at the housing, where the threshold force to detach the fixation element from the housing is chosen so high that such force levels would not occur during regular use of the oral hygiene implement.

The carrier element 210A may have a front carrier element 211A in which mounting holes 281A for mounting cleaning elements may be provided. The cleaning elements may be realized as bristle tufts that may be mounted by anchor tufting technology. In other embodiments, the cleaning elements may be realized as soft elastomeric elements, as movably mounted plastic elements etc. or as a mixture of different cleaning elements. In another embodiment, the carrier element may not be provided with any mounting holes but the carrier element may be provided with cleaning structures such as tongue cleaning structures.

The carrier element 210A has further a rear carrier element 219A. The front carrier element 211A and the rear carrier element 219A are connected via a connector carrier element 215A. The front carrier element 211A, the connector carrier element 215A, and the rear carrier element 219A may be realized as an integral element such as a plastic injection molded element, which shall not exclude that in other embodiments, that at least two of the three parts of the carrier element 210A are non-detachably snapped together or are screwed together or are glued together etc. When viewed in the direction of the rotation axis R, the front carrier element 211A and the rear carrier element 219A are arranged such that the rotation axis R extends through the front carrier element 211A and the rear carrier element 219A, while the connector carrier element 215A is arranged such that the rotation axis R extends through the cut-out or recess 216A provided in the carrier element 210A and does not intersect the connector carrier element 215A. The fixation element 230A extends through the cut-out or recess 216A such that the rotation axis R extends through the fixation element 230A.

The front carrier element 211A may have a blind hole 212A and the rear carrier 219A has a bore 218A that both extend along the rotation axis R and that both accommodate the axle 240A. In an embodiment as described above, in which the axle 240A is press-fitted into the bore 231A in the fixation element 230A and is as such fixed, the axle 240A may be loosely born in the blind hole 212A and the bore 218A (i.e. the blind hole 212A and the bore 218A form floating bearings of the axle 240A). The housing 290A may have a blind-hole 293A that extends along the rotation axis R and that accommodates the axle 240A. The axle 240A may be press-fitted into the blind-hole 293A. In another embodiment, the axle 240A may be fixedly secured at the carrier element 210A, for example, the axle 240A may then be press-fitted into the blind-hole 212A and the bore 218A and may be loosely born in the blind-hole 293A and the bore 231A.

By at least one or more of the features as described with respect to the example embodiment shown in FIG. 3, at least one of the following aspects is achieved. The axle 240A may be supported (in some embodiments pivot-mounted) at two locations at the carrier element 210A, which locations have a relatively large distance between each other. In particular, the two locations are arranged oppositely to each other with respect to the fixation element. This likely leads to a reduction of wobbling the carrier element 210A may experience during operation (i.e. when the carrier element 210A rotates or oscillates around the rotation axis R) in comparison to embodiments in which the axle would only be born at a single location. This becomes in particular relevant when the functional element is driven into a high rotation speed or a high frequency oscillation (for example, an oscillation frequency above about 80 Hz, above about 90 Hz, above about 100 Hz, above about 110 Hz, above about 120 Hz, above about 130 Hz, above about 140 Hz, above about 150 Hz etc.). In case a force F1 would be applied at the carrier element 210A in the direction of the rotation axis R to separate the carrier element 210A from the housing 290A, the fixation element 230A locks the carrier element 210A with respect to the housing 290A. It is very likely that only strong forces that would typically not be applied at the carrier element 210A during a typical oral hygiene operation could lead to a separation as the fixation element may in particular be non-detachably fixed at the housing 290A at two opposite locations.

In the embodiment shown in FIG. 3, a spring element 250A is arranged between the fixation element 230A and the rear carrier element 219A, thus biasing the carrier element 210A against the housing 290A. Such a biasing likely reduces clattering or rattling noises when the functional element is driven into motion as the unbiased carrier element would then tend to move up and down along the rotation axis in its floating bearings. In the shown example embodiment, the spring element 250A biases the carrier element 210A towards the rear of the housing 290A. Any additional force F2 that would be applied onto the carrier element 210A during operation by pressing the functional element 210A against a surface to be treated, for example, a tooth surface, would then act in the same direction and it is thereby avoided that the biasing spring force and the applied force F2 could cancel each other, which could then lead to rattling noises during operation. The spring element 250A may be realized as an integral part of the fixation element 230A. In some embodiments, the spring element is realized as an additional element, for example, a leaf spring, which spring may then be arranged between the fixation element and the rear carrier element. In some embodiments, the fixation element or the rear carrier element may comprise a stopper element to restrict the spring deflection and thus to avoid overstraining of the spring element, which may be in particular relevant when the spring element is an integral part of the fixation element, in particular in embodiments where the fixation element is a plastic part. In some embodiments, the housing 290A, the fixation element 230A, and the carrier element 210A may be made of any suitable plastic (for example, polypropylene, polyoxymethylene etc.) and the axle 240A may be made of metal such as steel. In such an embodiment, metal bushings may be fixedly secured in at least one of the blind hole 212A and the bore 218A (or in the bore 231A and the blind hole 293A) to avoid abrasion of the locations at which the axle is floatingly supported.

Figure 4A:
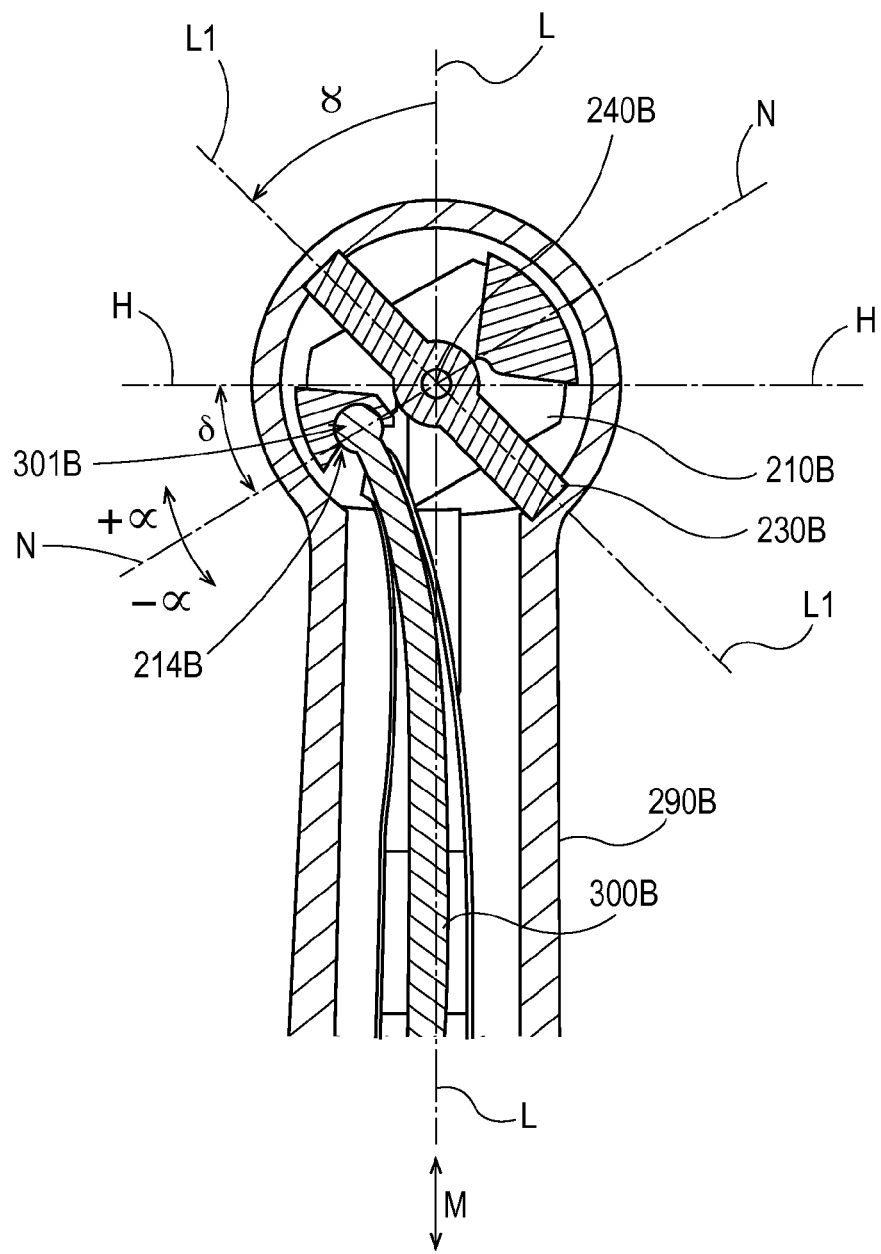
FIG. 4A is a lateral cross sectional cut through a head section of an example embodiment of an oral hygiene implement.

FIG. 4A shows a cross sectional cut through a head region of a further example embodiment of an oral care implement in accordance with at least one aspect of the present disclosure. The cut plane is oriented perpendicular to the rotation axis, i.e. perpendicular to the extension direction of the axle 240B. The housing 290B of the oral care implement may be essentially hollow and accommodates a shaft element 300B that may be a push rod, which shaft element 300B is attached at the carrier element 210B by means of a pivot pin 301B that extends into a elongated hole 214B provided in the carrier element 210B. The elongated hole 214B is provided eccentrically with respect to the axle 240B in the carrier element 210B. The shaft element 300B may be coupled to a drive provided in a housing of an oral hygiene device, which drive may linearly oscillate the shaft element 300B along the longitudinal extension axis L as is indicated by double arrow M with a peak amplitude value that may be in the range of between about ±0.1 mm to about ±1.0 mm. When the shaft element 300B is moved up and down along the longitudinal extension axis L, the pivot pin 301B induces an oscillation rotation of the carrier element 210B around the rotation axis defined by the axle 240B. The pivot pin 301B can freely rotate in the elongated hole 214B and it can move in sideward direction (i.e. in a direction parallel to the horizontal axis H) in the elongated hole 214B so that the shaft element 300B is not bent when it moves up and down.

In one embodiment, a fixation element 230B may be secured at the housing 290B at two oppositely lying locations. The fixation element 230B supports the axle 290B. The fixation element 230B may be essentially linearly extending along a direction L1 and is angled with respect to the linear extension direction L by an angle γ. If the angle γ would become smaller, the fixation element 230B could then not be secured at the housing 290B in the same manner as shown.

The shaft element 300B is shown in its neutral (or centre) position around which it will oscillate. Because of the inclination of the fixation element 230B against the longitudinal extension direction L, the neutral position of the pivot pin 301B is here inclined against the horizontal plane H by an angle δ. The horizontal plane H is perpendicular to the longitudinal extension direction L and extends through the axle 290B. When the shaft element 300B is linearly oscillated along the longitudinal extension axis L, this leads to an oscillation angle of ±α. As the neutral position of the pivot pin 301B is angularly offset from the horizontal plane H, the forces acting on the carrier element 210B via the pivot pin 301B are not symmetrical with respect to the neutral position.

Figure 4B:
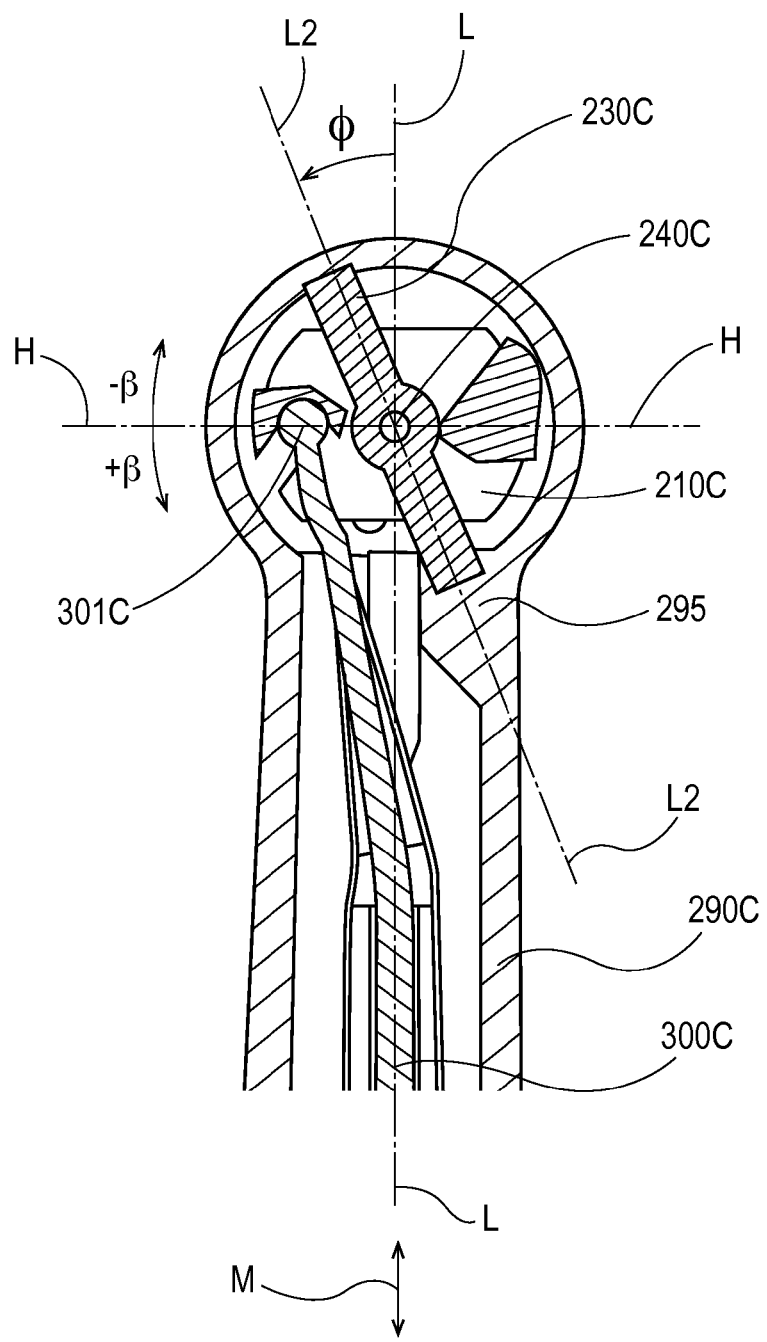
FIG. 4B is a lateral cross sectional cut through a head section of another example embodiment of an oral hygiene implement.

FIG. 4B shows a cross-sectional cut through another example embodiment of an oral hygiene implement. Here, the housing 290C has an inwardly extending thickened portion 295C. A fixation element 230C is secured at two opposite locations of the housing 290C and the fixation element 230C supports the axle 240C. The fixation element 230C is secured at the inwardly extending thickened portion 295C, which allows for a smaller angular offset φ between the extension direction L2 of the fixation element 230C and the longitudinal extension direction L. Because of this smaller angular offset, the neutral position of the pivot pin 290C can be located in the horizontal plane H that is perpendicular to the longitudinal extension direction L and that extends through the axle 290C. When the shaft element 300C is linearly oscillated along the longitudinal extension direction as indicated by double arrow M, then an oscillation angle ±β can be achieved, but where the forces that are applied at the carrier element 210C are more likely to be symmetric around the neutral position of the pivot pin 301C.

Figure 5A:
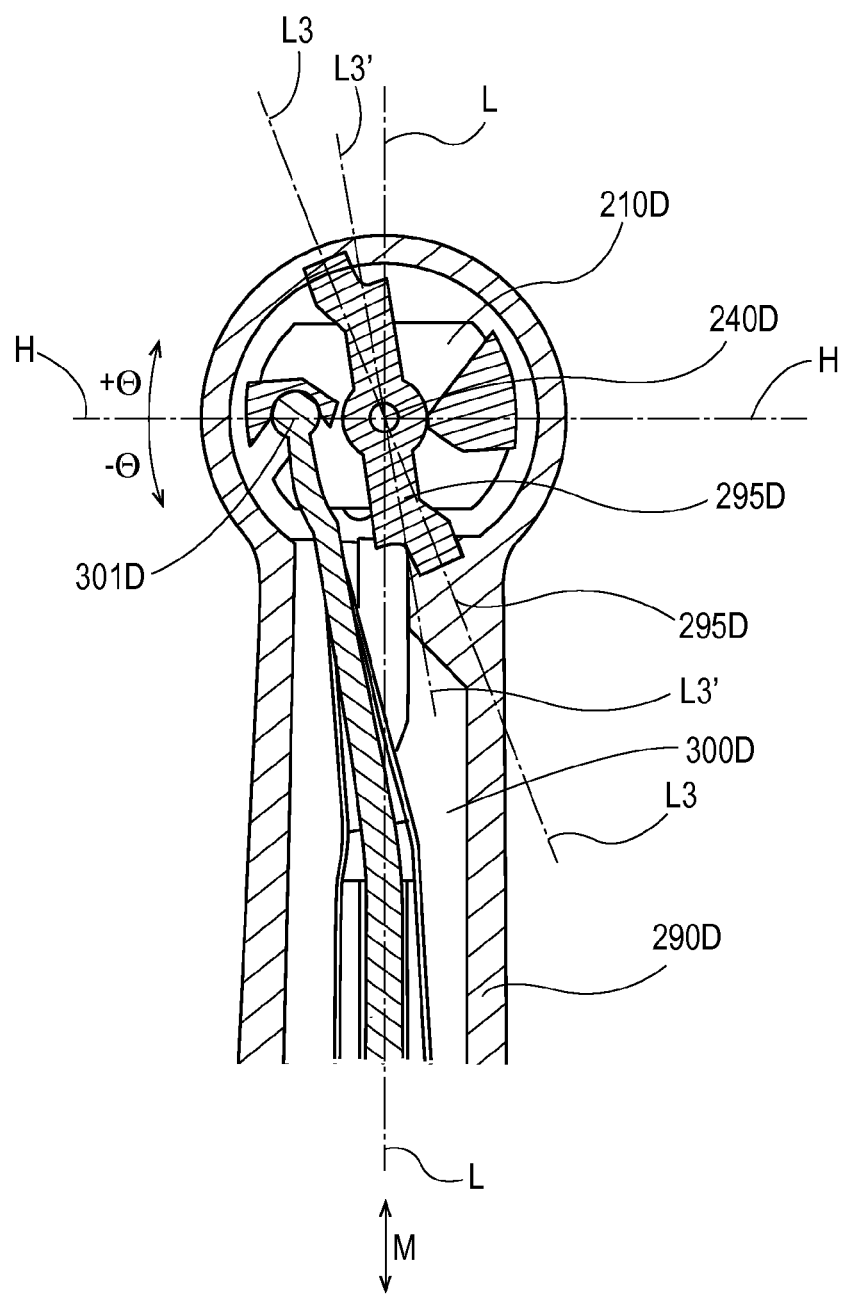
FIG. 5A is a lateral cross sectional cut through a head section of yet another example embodiment of an oral hygiene implement with a shaft element being in a neutral or rest position.

FIG. 5A shows a further cross-sectional cut through an example embodiment of an oral hygiene implement in accordance with the present disclosure. Here, a fixation element 230D is secured at the housing at two locations that are opposite with respect to the axle 290D that is supported in the centre of the fixation element 230D. As was shown also for the embodiment of FIG. 4B, the housing 290D has an inwardly extending portion 295D at which the fixation element 230D is supported to generally allow for a small angular offset between the general extension direction L3 of the fixation element 230D and the longitudinal extension direction L of the oral hygiene implement (the extension direction L3 is defined by the two mounting locations). In the shown embodiment, the fixation element 230D does not extend along the connecting line L3 between the two mounting locations. Instead, the fixation element 230D is curved in such a manner that it is concave with respect to the direction from which the pivot pin 301D approaches when moving in positive angular direction (i.e. toward the maximum oscillation angle +θ). This allows for a larger maximum oscillation angle as in the example embodiment shown in FIG. 4B. The effective extension direction of the fixation element 230D is indicated by L3'. As is shown in FIG. 5A, the fixation element 230D may be symmetrically curved with respect to the centre axis defined by the axle 290D. Here, curved shall include stepped designs of the fixation element 230D. As in the embodiment shown in FIG. 4B, a pivot pin 301D of a shaft element 300D is coupled to a carrier 210D of the functional element of the oral hygiene implement in the horizontal plane H when being in the neutral position.

Figure 5B:
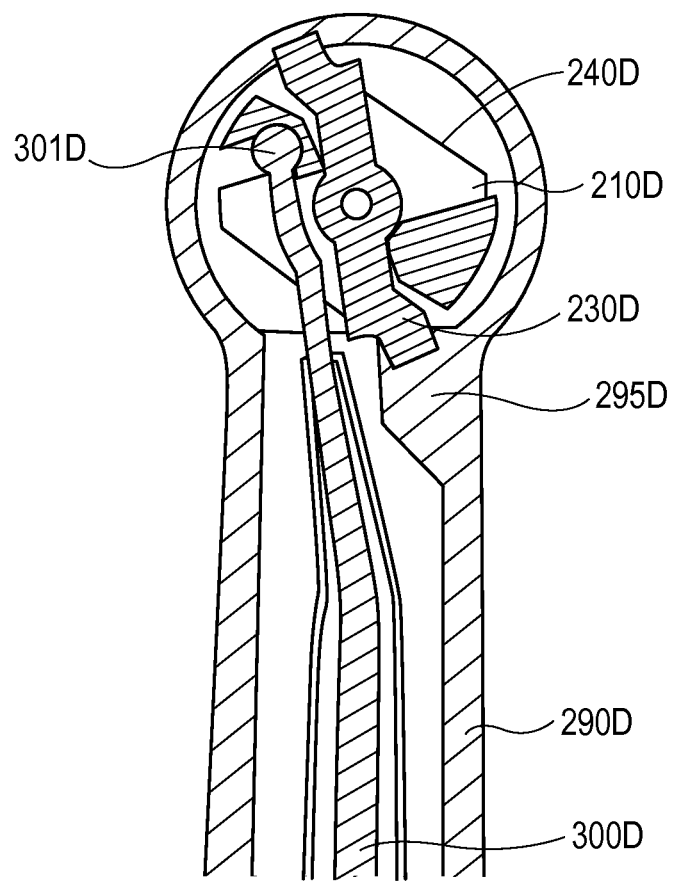
FIG. 5B is a lateral cross sectional cut through a head section of the oral hygiene implement shown in FIG. 5A but with the shaft element being in a maximally deflected position.

FIG. 5B is a cross sectional cut of the oral hygiene implement shown in FIG. 5A but with the pivot pin 301D being in its maximally deflected position. Due to the curved realization of the fixation element 230D, the maximally deflected position allows for a larger oscillation angle of the carrier element 210D than in the embodiment shown in FIG. 4B.

Figure 6:
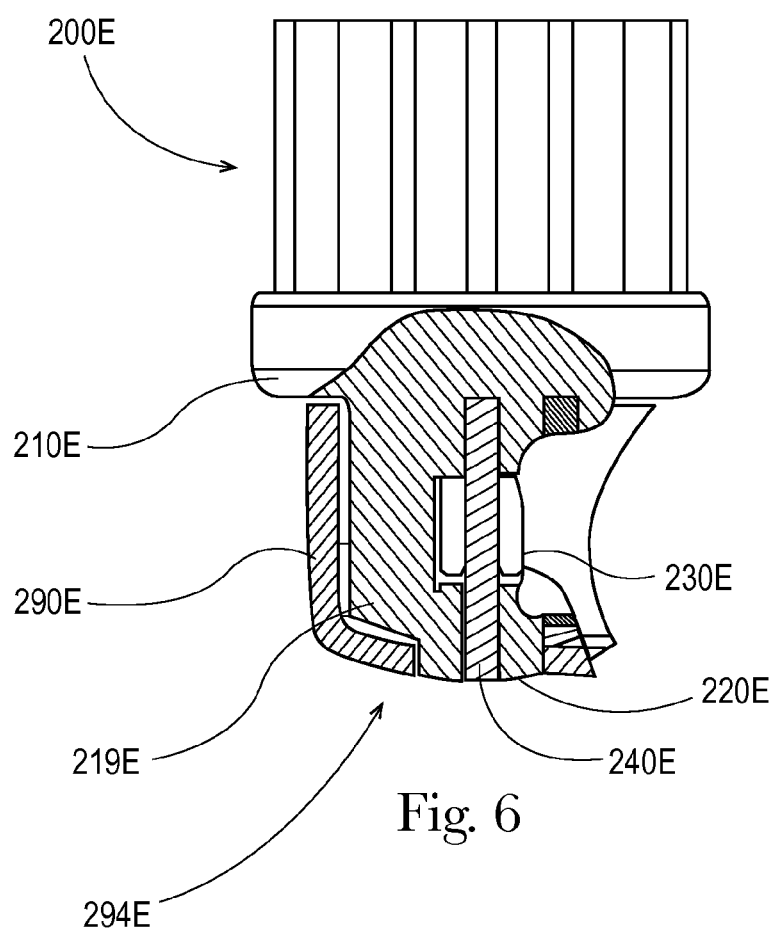
FIG. 6 is a partly cut open depiction of a further example embodiment of an oral hygiene implement.

FIG. 6 is a partly cut open further embodiment of an oral hygiene implement. In this embodiment, the carrier element 210E of the functional element 200E has a portion 220E that extends through an opening 294E in the housing 290E of the oral hygiene implement. The extending portion 220E may be realized as an integral part of the rear carrier element 219E. The outer surface of the extending portion 220E may smoothly join with the outer surface of the housing 290E. Thus, the extending portion 220E may serve as a mounting structure for mounting the functional element 200E at the housing 290E and it may further serve to add a more aesthetic function in case that the housing 290E and the extending portion 220E have e.g. different colors. In such an embodiment, the axle 240E may be press fitted into the carrier element 210E and may be floatingly born by the fixation element 230E.

It is to be noted that the various features that have been described in combination with other features for the different embodiments are meant to be disclosed as individual feature that shall be considered as being disclosed in all possible combinations with all other features as long as this does not contradict the gist and scope of the present disclosure.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral hygiene implement comprising:
a housing;
a movably mounted functional element;
a fixation element that is secured at the housing and that essentially locks the functional element at the housing; and
an axle that is supported by the fixation element,
wherein the functional element is arranged for movement around the axle; and wherein the fixation element extends through a cut-out or recess provided in a carrier element of the functional element, such that pulling the functional element out of the housing along the longitudinal axle extension direction is inhibited, wherein the axle is supported at two locations provided at the carrier element, wherein the two locations are disposed on opposite sides of the fixation element.

2. The oral hygiene implement according to claim 1, wherein the fixation element and the housing are non-detachably connected.

3. The oral hygiene implement according to claim 1, wherein a shaft element is coupled to the functional element, the shaft element being arranged to drive the functional element into motion around the axle during operation.

4. The oral hygiene implement according to claim 3, wherein the shaft element is eccentrically coupled to the functional element such that in a neutral position the coupling location lies in a plane going through the axle and being perpendicular to a longitudinal extension axis of the oral hygiene implement.

5. The oral hygiene implement according to claim 1, wherein the fixation element is at least partly curved between a location where the fixation element is secured to the housing and a location where the axle is supported by the fixation element.

6. The oral hygiene implement according to claim 1, wherein a spring element is arranged between the carrier element and the fixation element, such that the spring element biases the carrier element in a direction that essentially coincides with the direction of a load that would be applied onto the functional element during operation when the functional element is pressed against a surface.

7. The oral hygiene implement according to claim 6, wherein the spring element is an integral part of the fixation element.

8. The oral hygiene implement according to claim 1, wherein a portion of the functional element extends through an opening provided in the housing, the extending portion being different to a primary functional portion of the functional element and being disposed opposite to the primary functional portion.

9. The oral hygiene implement according to claim 1, wherein the housing has an inwardly thickened portion at which the fixation element is secured.

10. The oral hygiene implement according to claim 1, wherein the oral hygiene implement is a powered oral hygiene device having a drive unit arranged to drive the functional element into a movement around the axle during operation.

11. The oral hygiene implement according to claim 1, wherein the oral hygiene implement is a detachable brush for an electric toothbrush.

12. An oral hygiene device comprising a handle and an oral hygiene implement according to claim 1, that is detachably attached to the handle.

* * * * *